United States Patent
Gray et al.

(10) Patent No.: US 9,864,780 B2
(45) Date of Patent: *Jan. 9, 2018

(54) GAIT-BASED BIOMETRIC DATA ANALYSIS SYSTEM

(71) Applicant: AUTONOMOUS ID CANADA INC., Ottawa (CA)

(72) Inventors: Todd Gray, Ottawa (CA); Vladimir Polotski, Ottawa (CA); Barry Smale, Ottawa (CA); Bernard F. Grisoni, Cordova, TN (US); Erik Mettala, Finksburg, MD (US)

(73) Assignee: AUTONOMOUS_ID CANADA INC., Ottawa, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/946,358

(22) Filed: Nov. 19, 2015

(65) Prior Publication Data
US 2016/0147841 A1 May 26, 2016

Related U.S. Application Data

(63) Continuation-in-part of application No. 13/939,923, filed on Jul. 11, 2013, now Pat. No. 9,204,797, which
(Continued)

(51) Int. Cl.
*A61B 5/103* (2006.01)
*G06F 17/30* (2006.01)
(Continued)

(52) U.S. Cl.
CPC ...... *G06F 17/30528* (2013.01); *A43B 3/0005* (2013.01); *A61B 5/1038* (2013.01);
(Continued)

(58) Field of Classification Search
CPC ... A61B 5/1036; A61B 5/1038; A61B 5/4528; A61B 5/1071; A61B 5/103
(Continued)

(56) References Cited

U.S. PATENT DOCUMENTS

| 4,812,976 A | 3/1989 | Lundy |
| 6,183,425 B1 * | 2/2001 | Whalen ............... A61B 5/1038 600/592 |

(Continued)

FOREIGN PATENT DOCUMENTS

| WO | 2004021883 A1 | 3/2004 |
| WO | 2004092915 A2 | 10/2004 |
| WO | 2010096907 A1 | 9/2010 |

OTHER PUBLICATIONS

Kong, Kyoungchul et al., "A Gait Monitoring System Based on Air Pressure Sensors Embedded in a Shoe", IEEE/ASME Transactions on Mechatronics, vol. 14, No. 3, Jun. 2009.
(Continued)

*Primary Examiner* — Daniel Cerioni
(74) *Attorney, Agent, or Firm* — Brion Raffoul

(57) ABSTRACT

Systems and methods for diagnosing a user's condition based on his gait. A sensor module with multiple sensors is placed inside a user's shoe and biometric data is gathered from the sensors when the user takes a step or walks. The data is used to generate loops as the various sets of data is plotted against each other. The loops obtained from the data are then compared against stored loops previously obtained. Based on the results of the comparison, the user's condition is diagnosed using predetermined indicators of specific health issues. Using the biometric data and in conjunction with data from various databases, it can be determined whether the user has a specific condition, whether a specific condition is worsening, or whether a specific condition is improving.

8 Claims, 9 Drawing Sheets

Related U.S. Application Data is a continuation-in-part of application No. 13/581,633, filed on Dec. 6, 2012, now Pat. No. 9,188,963.

(51) Int. Cl.
*A61B 5/00* (2006.01)
*A43B 3/00* (2006.01)
*A61B 5/11* (2006.01)

(52) U.S. Cl.
CPC ............ *A61B 5/112* (2013.01); *A61B 5/6807* (2013.01); *G06F 17/30554* (2013.01); *A61B 2562/046* (2013.01)

(58) Field of Classification Search
USPC .................................................. 600/592, 595
See application file for complete search history.

(56) References Cited

U.S. PATENT DOCUMENTS

| | | | |
|---|---|---|---|
| 6,360,597 | B1 | 3/2002 | Hubbard |
| 2002/0107649 | A1 | 8/2002 | Takiguchi et al. |
| 2004/0228503 | A1* | 11/2004 | Cutler ............... G06K 9/00348 382/103 |
| 2005/0288609 | A1 | 12/2005 | Warner et al. |
| 2006/0080551 | A1 | 4/2006 | Matyjarvi et al. |
| 2006/0287883 | A1* | 12/2006 | Turgiss ............... G06F 19/3418 705/2 |
| 2007/0021689 | A1* | 1/2007 | Stergiou ............... A61B 5/1038 600/595 |
| 2008/0287832 | A1 | 11/2008 | Collins et al. |
| 2009/0058855 | A1 | 3/2009 | Mishra et al. |
| 2010/0324455 | A1 | 12/2010 | Rangel et al. |
| 2011/0282828 | A1 | 11/2011 | Precup et al. |
| 2012/0086550 | A1 | 12/2012 | Leblanc et al. |

OTHER PUBLICATIONS

Yamakawa, Takeshi et al., "Biometric Personal Identification Based on Gait Pattern Using Both Feet Pressure Change", Automation Congress, 2008. WAC 2008. World, pp. 1-6, Sep. 28-Oct. 2, 2008.

Huang, Bufu et al., "Gait Modeling for Human Identification", 2007 IEEE International Conference on Robotics and Automation, Roma, Italy, Apr. 10-14, 2007.

Chedevergne, Fany et al., "Development of a Mechatronical Device to Measure Plantar Pressure for Medical Prevention of Gait Issues", Proceedings of the 2006 IEEE International Conference on Mechatronics and Automation, Jun. 25-28, 2006, Luoyang, China.

Boulgouris et al, "Biometrics: Theory, Methods, and Applications", Wiley-IEEE, Nov. 2009, Chapter 18.

Morris, Stacy et al., "Shoe-Integrated Sensor System for Wireless Gait Analysis and Real-Time Feedback", Proceedings of the Second Joint EMBS/BMES Conference, Houston, TX, Oct. 23-26, 2002.

Gafurov, Davrondzhon et al., "Biometric Gait Authentication Using Accelerometer Sensor", Journal of Computers, vol. 1, No. 7, Oct./Nov. 2006.

International Searching Authority, International Search Report for PCT/CA2010/001002.

Office Action on corresponding Canadian Patent Application No. 2,791,401.

* cited by examiner

GAIT-BASED BIOMETRIC DATA ANALYSIS SYSTEM

RELATED APPLICATIONS

This application is a Continuation-in-Part of U.S. patent application Ser. No. 13/939,923 filed Jul. 11, 2013, which is a Continuation-in-Part of U.S. Pat. No. 9,188,963 filed Dec. 6, 2012.

TECHNICAL FIELD

The present invention relates to a gait based biometric data analysis system used for the detection and isolation of individual and for general population movement and mobility biomarkers and cause determination of the progression or regression of health, wellness and fitness along with known pathological conditions associated with disease states and the effects of prescribed pharmacological and therapeutic treatments. More specifically, the present invention relates to an analytical system based on biometric loop signature formation with data analysis being performed in conjunction with an insole insert in a shoe for personalized analytics or in a populated data system for movement and mobility research in general.

BACKGROUND

The increase in activity in the personal wellness and fitness, mobile healthcare and user discrete analytical fields have highlighted some shortcomings of current personal and population based analytics systems as well as the effects of generally prescribed pharmacological and therapeutic treatments after diagnosis.

Analytical systems generally come in a number of categories. Data, text and imaging systems use large installed or network based hardware and software platforms which, when used, diagnoses the user's condition using artificial intelligence, machine learning and other techniques common to those systems and methods. Less cumbersome and intrusive analytical systems and methods include question and answers done orally or written, which measure temperature, weight, pulse rate, as well as a plethora of other biological and physiological indicators. These indicators are used when searching for signs of health, fitness level, and disease. The ancient medicinal art of reflexology has historical efforts focused on disease pathology and the feet. Adverse reactions to prescribed pharmacological and therapeutic treatments of disease are known to adversely affect a person's balance and, as a consequence, that person's gait as well.

The above noted analytical systems have their drawbacks. Specifically, artificial intelligence, machine learning and other techniques common to those systems and methods are extremely large and use controlled or proprietary software algorithms. Similarly, question and answers obtained orally or in written form are area specific, limited in scope and use, and require more active participation and knowledge from the user. These and other current systems have been seen as either too invasive, too cumbersome for some people to use and too complicated to understand.

There is therefore a need for an analytical system that is neither invasive nor linear in scope and use and which provides access to data gathered by convenient user-worn devices.

SUMMARY

The present invention provides analytical systems and methods for the assessment of movement and mobility based on gait. A sensor module with multiple sensors is placed inside a user's shoe and biometric data is gathered from the sensors when the user takes a step or walks. The data is used to generate loops as the various sets of data are plotted against each other to form a loop based biometric of a user. The loops obtained from the data are then compared against stored loops previously obtained as well as other characteristic data extrapolated from the loops. Based on the results of the comparison, the user's movement and mobility characteristics are assessed using predetermined indicators in conjunction with analytical input from distributed databases and with the input of each user's specific characteristic data from which other data can be extrapolated. Using the biometric data, it can be determined whether the user has increased activity and performance or whether the user has the proper fitting insole insert and, if not, recommendations for production alteration can be made. Similarly, the data gathered can be used to determine whether the footwear the user is using is of a proper fit or whether recommendations for alternative footwear types and models is warranted. As well, the data and the system can be used to determine whether the user has a specific condition or ailment, whether a specific condition or ailment is worsening, or whether a specific condition or ailment is improving.

In one embodiment, the user's biometric data is, preferably, previously extracted from his gait. The previously gathered data, and the plotted loops derived therefrom, can be used as a baseline for the user. Subsequent biometric data sets gathered from the user can then be compared against the baseline. Depending on the comparison results, a range of analysis can be performed including progression or regression of a user's movement and mobility can be determined. Data gathered from the general population can be used to establish any correlation between a person's changing gait as he or she progresses or regresses in a specific health and fitness condition. Treatment effects of prescribed pharmacological and/or therapeutic remedies can also be determined using the baseline biometric data from the user as the user progresses in his or her daily programs and treatment. Periodic gathering of the user's biometric data can be used to track and monitor the effects of the treatment on the user's gait to establish any causal link between the treatment regime and the user's gait. Such links and the specific effects of the fitness program or treatment regime can then be used to further heighten the effectiveness of shoe based biometric data gathering devices as diagnostic tools. In addition to the above, the diagnostic tools can be supplemented by a network of distributed databases that have pathomechanical movement and mobility data. Such data, in conjunction with data received from an insole and with a user's specific characteristics, can for example be used to narrow down a suitable diagnosis for the user's pathomechanical abnormality. Such network of distributed databases storing a population of movement and mobility data and related characteristic data such as foot shape, foot type, standing weight and posture can for example be used to narrow down gait based movement and mobility biomarkers associated to a range of performance, human ailments and disease.

In a first aspect, the present invention provides a method for determining changes in a user's movement and mobility using a foot-based gait device, said device having a plurality of sensors for gathering gait-based data, the method comprising:

a) selecting two of said plurality of sensors;
b) gathering data from each sensor selected in step a);

c) correlating data gathered from said two sensors such that data points gathered at similar instances are matched with one another to result in data pairs;

d) determining at least one characteristic loop from said data pairs, each characteristic loop being a loop formed when said data point pairs are plotted;

e) retrieving signature characteristic data, said signature characteristic data being derived from data resulting from biometric data previously gathered from said user;

f) determining a signature characteristic loop from said signature characteristic data;

g) comparing characteristics of said at least one characteristic loop determined in step d) with characteristics of said signature characteristic loop determined in step f);

h) in the event a comparison of said characteristics compared in step g) produces results not within predetermined limits, determining that a change has occurred in said user's gait-based biometric data;

i) in the event a comparison of said characteristics compared in step g) produces results within predetermined limits, determining that a change has not occurred in said user's gait-based biometric data.

In a second aspect, the present invention provides a system for diagnosing a change in a user's gait-based biometric data, the system comprising:

a sensor module comprising at least one sensor for gathering gait-based biometric data from said user a data storage module for storing data relating to a signature loop, said signature loop being a loop resulting from a plot of data pairs derived from data gathered from said sensor module when said user uses said system a data processing module for receiving data from said sensor module, said data processing module being for determining characteristic loops from said data received from said sensor module and for comparing characteristics of said characteristic loops with characteristics of said signature loop wherein a change in said user's gait-based biometric data is indicated when said characteristics of said characteristic loops are not within predetermined limits of said characteristics of said signature loops.

In a third aspect, the present invention provides for use of an insole for use with a user's shoe to determine if a change has occurred in a user's gait-based biometric data, said insole comprising a plurality of sensors for measuring and detecting force applied by said user on different parts of said insole.

In a fourth aspect, the present invention provides for a network of distributed databases storing populated characteristic data for individual, group and general analytical insights in human movement and mobility.

BRIEF DESCRIPTION OF THE DRAWINGS

The embodiments of the present invention will now be described by reference to the following figures, in which identical reference numerals in different figures indicate identical elements and in which.

DETAILED DESCRIPTION

The present invention, in one aspect, provides systems and methods relating to an intelligent analytical system which uses user discrete characteristic data acquired from wearable and other mobile devices. The system has biometric authenticated data integrity, allows for personalized, group or population based analysis of characteristic data and is not vulnerable to legacy computing systems, power failures, or unauthorized system access. The system, especially the server connected to multiple health or fitness based databases, has the facility and learning capacity to assess and analyze a user's unique biometric loop signature data and other characteristics extrapolated from such loop signature data such as step count, step and stride length, stride to stride variability, and center of force at any time interval for comparison against stored user data. The analytical system has the capability for targeted analysis of groupings of populated data characteristics such as gender, nationality, age, height, weight, foot shape such as Germanic or Celtic, foot type such as high arch or flat arch, posture, health and fitness. This analysis may be performed for research in movement and mobility biomarkers.

Figure 1:
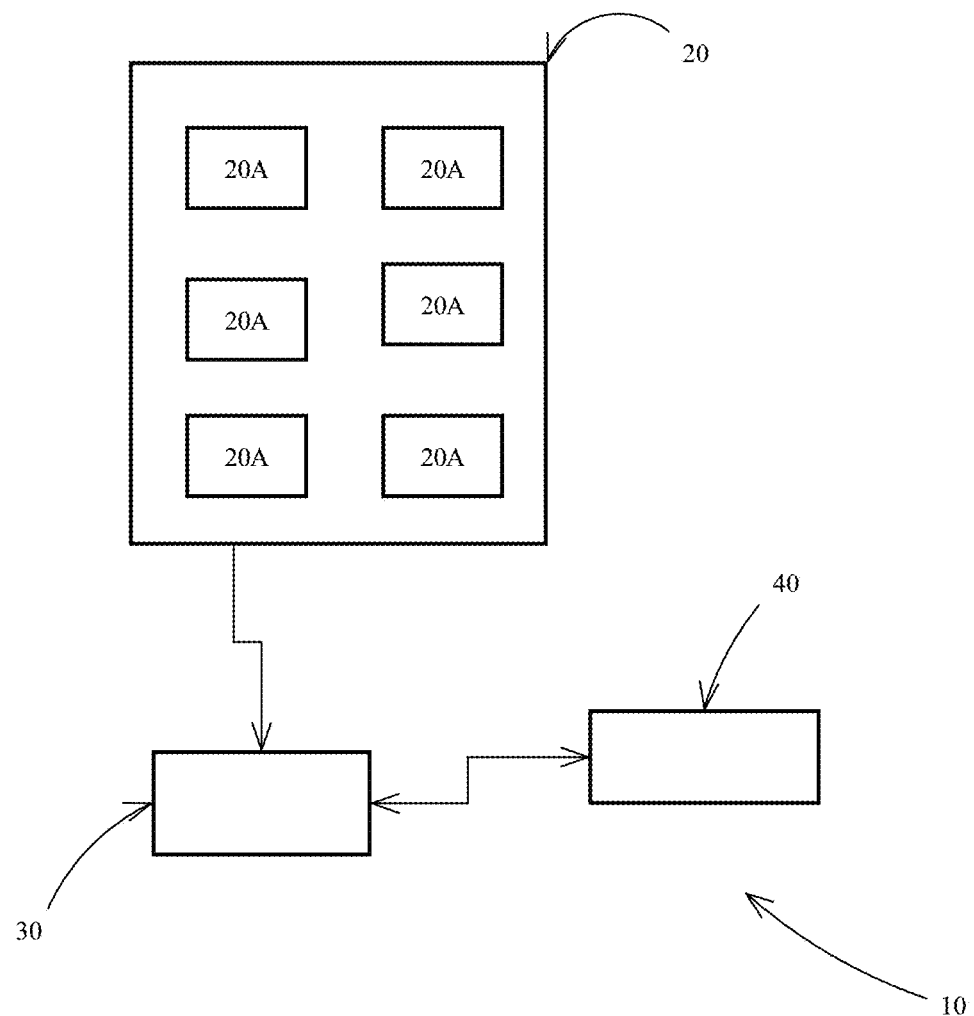
FIG. 1 is a block diagram of the system according to one aspect of the invention.

Referring to FIG. 1, a block diagram of one embodiment of the present invention is illustrated. As can be seen, the system 10 includes a sensor module 20 coupled to a data processing module 30 and which may receive data from a storage module 40. In broad terms, the sensor module 20, having multiple sensors 20A, generates biometric data from the sensors (biometric data based on the user's gait) which is then sent to the data processing module 30. The data processing module 30 then processes the biometric data and retrieves signature data from the storage module 40. The signature data comprises data that was previously gathered from the user who is currently being diagnosed. The data processing module then compares the signature data with the biometric data gathered from the multiple sensors. If there are differences between the newly gathered data and the previously gathered data, the data processing module then determines if the differences are in line with known patterns which would indicate progression or regression of known user conditions. This conclusion would be based on gait-based biometric data which would indicate an improvement or decline in health and fitness or new health conditions.

As well, the system includes a communications module 50 that is coupled to the data processing module 30. The communications module 50 sends and/or receives communications regarding the comparison between the signature data and the data gathered from the sensors. The communications module 50 sends the data gathered to the data processing module 30 such that further data processing is performed remote from the user and/or the sensor module 20. The further data processing may be performed by a personal mobile device or by a server remote from the user's location and coupled to a network of distributed databases. By off-loading most of the post biometric authentication processing to a personal mobile device or to the remote server, the insole system does not need much processing capability.

It should be noted that the sensor module 20 has multiple sensors which gather data regarding a person's gait as well as other discrete user characteristics such as weight, stride length, and stride to stride variability. In one embodiment, the sensor module is an insole positioned inside the user's shoe, with the insole having multiple discrete force sensors that detect the amount of force or pressure exerted on a section or region of the insole. With multiple regions on the insole and at least one sensor positioned on each region, a user's gait can be profiled as being the amount of pressure that that user exerts on each region over time as the user takes a step. A variant of this sensor module would have at least one strain gauge positioned such that the pressure exerted on each of the multiple regions of the foot are detected by the gauge with each region corresponding to a section of the strain gauge. With such an arrangement, each section of the strain gauge thus acts as a different discrete sensor.

It should be noted that, in one embodiment, two insoles are used per user. This way, gait data may be gathered for each user foot. Data gathered from the user's left foot may be processed differently from data gathered from the user's right foot. The data gathered from each foot may then be combined to determine characteristics such as, for example, step count, cadence, velocity, and stride length. Alternatively, another embodiment only uses a single insole such that only one set of data is gathered per user. While the description below relates to a single insole, for a two insole embodiment, both insoles would be similar to one another and would, preferably, each conform to the description and principles outlined below.

Figure 2A:
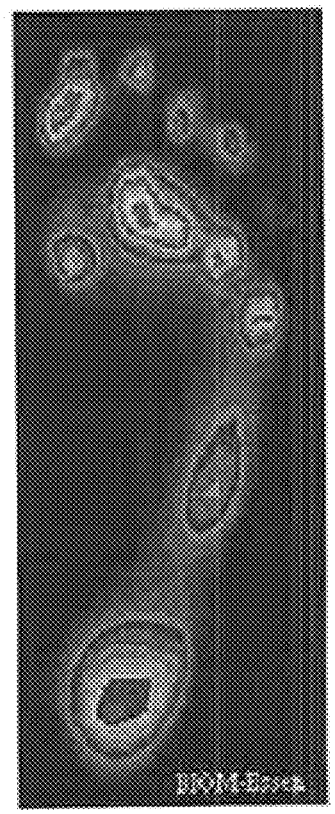
FIG. 2A is an image illustrating the different forces applied by a human foot as it takes a step.
Figure 2B:
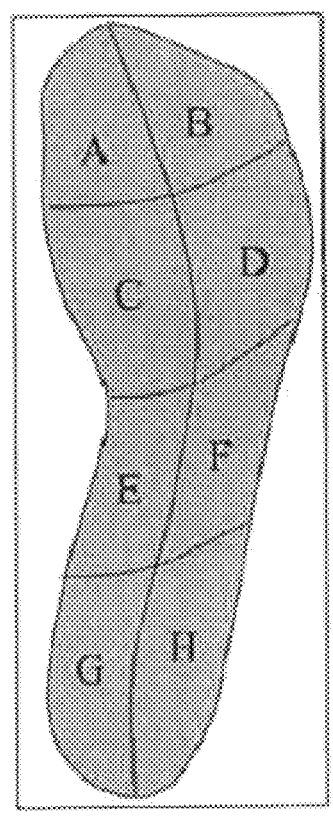
FIG. 2B is a diagram illustrating different zones on an insole according to one embodiment of another aspect of the invention.

Referring to FIGS. 2A and 2B, a schematic illustration of a number of discrete pressure zones on an insole is illustrated. FIG. 2A shows an imprint of a human foot and the unique pressure points for a specific person. FIG. 2B illustrates the location of 8 specific pressure zones or areas on one embodiment of a pressure sensing insole. Each zone in FIG. 2B has a pressure sensing pad or sensor assigned to it such that the pressure exerted on each zone can be measured. A variant of this sensor module would have, instead of discrete sensor pads at each zone, a single strain gauge positioned as described above.

In the above embodiment, each sensor in the sensor module produces a signal linearly proportional to the force being applied to the sensor. Preferably, each sensor or zone would have a data channel dedicated to its readings for transmitting those readings to the data processing module. Alternatively, in one implementation, the readings can be time division multiplexed on to a single data line from the sensor module to the data processing module. In this implementation, the data is passed through a single A/D converter to produce multiplexed channels, one for each sensor. Of course, while there are eight zones in FIG. 2B, other variants may have more or less than eight zones.

Regarding the data stream produced when the user is walking, in one embodiment, each sensor produces several hundred samples equating to approximately ten steps taken by the user. This data stream is then saved and examined by the data processing module and the actual step points are determined. Each step is identified and the saved data stream resampled at a precise rate of approximately 100 samples per step.

It should be noted that multiple parameters regarding the user's gait can be extracted from the data produced by the sensor module depending on the type of sensors used in the sensor module. These parameters can then be used as points of comparison with the signature (or characteristic) data mentioned above. Some of these parameters may be:

Actual forces
Relative (normalized) forces.
Ratios between the peak forces in the eight sensor zones
Relative timing between forces on each sensor (strike and release sequence)
Average rate of change of force on each sensor zone
Maximum rate of change of force on each sensor zone
Frequency spectrum of the waveform from each sensor (ratio of values of harmonics derived from a Fourier transform)
Heel strike and toe lift off impact forces in the three axes.
Data waveform shape matching (waveform shape matching)

The parameters extracted from the data stream may then be compared directly or indirectly with the signature data noted above.

In one comparison scheme, the parameters extracted are used to derive a shape or loop, the characteristics of which can the compared with characteristics of a signature loop or shape. The use of a loop or shape allows for an indirect comparison between the data read by the sensor module and the signature or characteristic data. As well, it allows for more complex comparison schemes and for easier use of tolerances in the comparison.

For this comparison scheme, data from two different sensors are read by the data processing module. The two data sets (one from a first sensor and a second from a second sensor) are correlated with one another to synchronize the readings. This is done so that the data readings are synchronized in their time indices. Once synchronized, readings taken at approximately the same time index are matched with one another. Thus the result is that a data reading from sensor A taken at time t1 is mated with a data reading from sensor B taken at time t1. The mating step results in a set of pairs of data readings from two different sensors.

It should be noted that a preferable preliminary step to the correlation step is that of applying a low pass filter to both sets of data. Such a low pass filter would remove the low frequency components of the signals and would provide cleaner and easier to process signals.

As an example of the processing performed on the data streams received from the sensor modules, FIGS. 3-8 are provided to aid in the understanding of the process. Prior to any processing, data streams are first received from all of the sensors for a given fixed duration. For each sensor, the data stream for the given duration is saved by the data processing module. The resulting waveform for each sensor is then partitioned to determine discrete steps taken by the user. If the sensors are force/pressure sensors, this partitioning may be done by searching for peaks and valleys in the waveform. Each peak would denote a maximum force applied to the sensor and each valley would denote a minimum (if not absence) of force. Each step can then be seen as two valleys with a peak in between, representing the user's foot in the air, the actual step, and then user lifting his/her foot again.

Alternatively, depending on how the system is configured, each step might be seen as two peaks bookending a valley.

Figure 3:
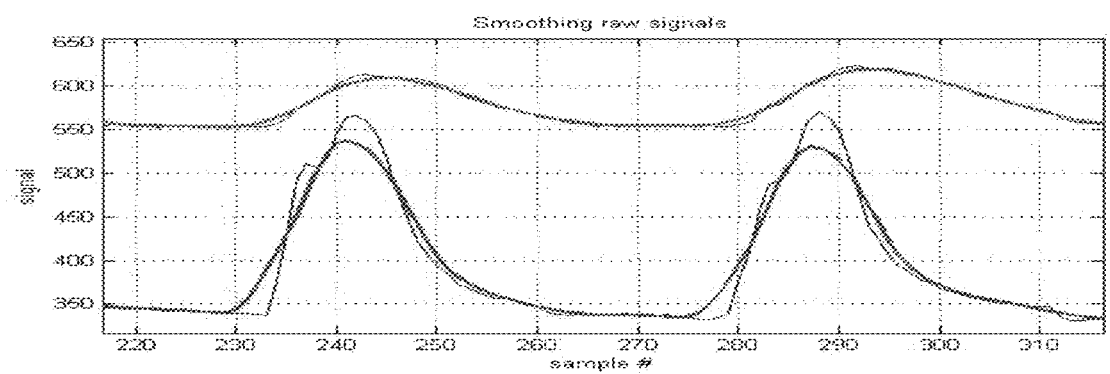
FIG. 3 illustrates raw data waveforms and data waveforms after a low pass filter has been applied.

Referring to FIG. 3, two raw data streams is shown at the bottom of the plot. After a low pass filter is applied to the signals, the smoother waveforms are shown at the top half of FIG. 3. From FIG. 3, one can see maximum force applied to the force pads for the two steps captured by the waveforms.

Once the discrete steps have been delineated in the data received from each of the sensors, each step for each sensor is then resampled to arrive at a predetermined number of data samples for each step. For the resampling, each sample is for a predetermined time frame and at a predetermined point in time in the current step. As an example, if each step lasts approximately 0.1 sec and 100 samples per step are desired, then the first sample is taken at the first one thousandths of a second in the waveform and the second sample is taken at the second one thousandths of a second and so on and so forth. This method essentially synchronizes all the samples such that it would be simple to determine all samples (from all the sensor readings) taken at the first one thousandths of a second or all samples taken at the first fiftieth one thousandths of a second as the relevant samples would all be similarly time indexed.

Once the different data waveforms from the different sensors have been synchronized, any two of the sensors and the data they produced can be selected for comparison with the signature data noted above and which may be stored in the data storage module. Depending on the configuration of the system, the signature or characteristic data stored in the data storage module may take numerous forms. In one example, multiple data sets/pairs (either filtered or as raw data) from the user may be stored so that a signature loop may be derived from the signature data whenever the characteristics of that signature loop are required. For this example, all the data pairs from all sensors would be stored so that any two sensors may be selected. Alternatively, the specific characteristics of the signature loop may be stored as the signature or characteristic data if one wanted to dispense with determining the signature loop every time a comparison needs to be made. As another alternative, only the data relating to the average signature loop derived from the user may be stored as signature data. Of course, if multiple sensors are to be used, then most possible average signature loops from the user data would be stored. In one other alternative, all the raw data (either filtered or not) from the user's steps may be stored as signature data. Such a configuration would allow for the greatest amount of flexibility as the system could randomly select any two of the sensors to be used and the signature data from the user would be available for those two sensors. As noted above, this configuration would require that the signature loop be calculated every time a comparison is required. The signature data may, if desired, be stored in encrypted format.

Once two of the sensors are selected from the sensors available in the sensor module (in this example the sensor module has 8 sensors, one for each of the eight zones illustrated in FIG. 2B), the resampled data for those two sensors are then mated with one another. This means that each time indexed sampling will have two points of data, one for the first sensor and another for the other sensor. These pairs of sensor readings can thus be used to create a characteristic loop. As an example, if sensors A and B are used and n denotes an index, then A[n] denotes the nth sampled reading from the waveform received from sensor A for a specific step. Similarly, B[n] is the nth sampled reading from the waveform received from sensor B for the same specific step. {A[n], B[n]} thus constitutes a data pair for the nth reading for that particular step. Plotting all the data pairs for a particular step, with readings from one sensor being on one axis and readings from the other sensor on the axis, results in an angled loop-like plot (see FIGS. 4-8 as examples). For pressure/force readings, this is not surprising as the force exerted by the foot in a particular step increases to a maximum and then decreases to as minimum as the person increases the weight the place on the foot and then removes that weight as the step progresses.

Figure 4:
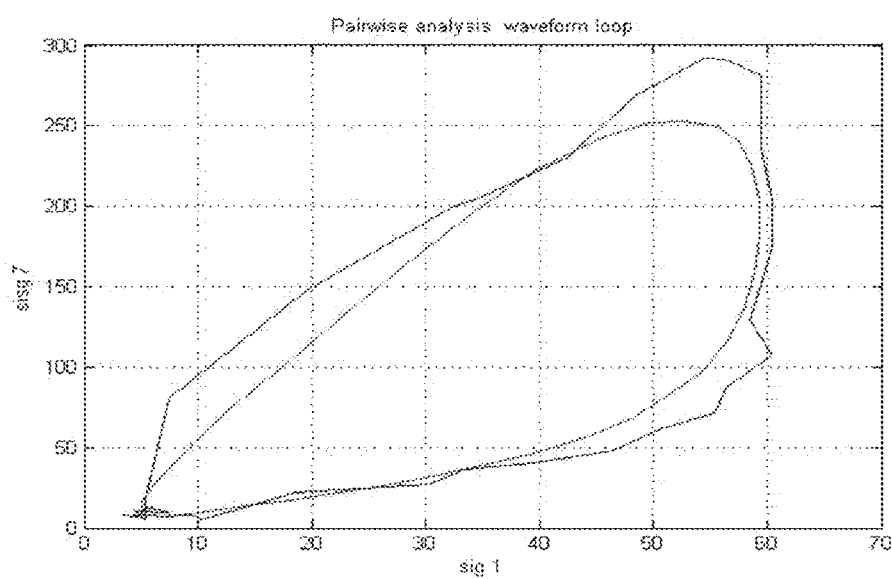
FIG. 4 illustrates loops plotted using raw data and filtered data.

Once the data pairs have been created, a plot of the resulting loop can be made. As noted above, FIG. 3 shows the waveforms for two signals—the lower waveform being the raw data stream waveforms for 2 signals and the upper waveforms for the same 2 signals after a low pass filter has been applied. FIG. 4 shows a plot of the two sets of waveforms in FIG. 3. One loop in FIG. 4 is derived from the raw signal waveforms in FIG. 3 while the other loop is derived from the low pass filtered waveform in FIG. 3. As can be seen in FIG. 4, a smoother loop is produced by the low-pass filtered signals. It should be noted that the x-axis in FIG. 4 contains the values gathered from the first sensor selected while the y-axis contains the values gathered from the second selected sensor. It should be noted that while the embodiment discussed uses only a pair of sensors, the concept is applicable for 3, 4, or any number of sensors. If data from 3 sensors were used, then, instead of a 2D loop, a 3D loop may be created as a characteristic loop.

Figure 5:
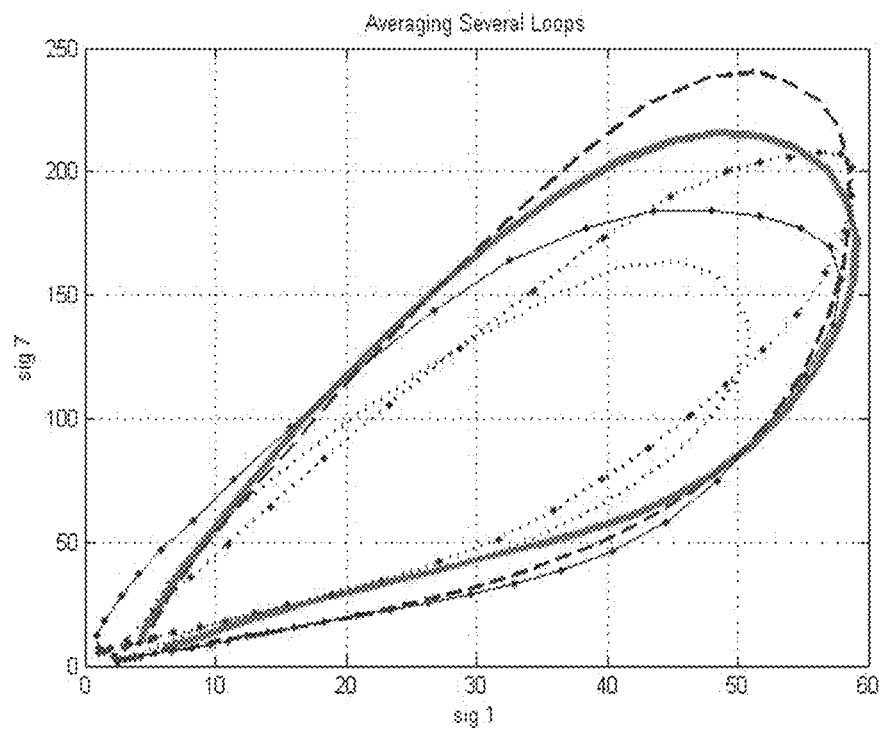
FIG. 5 illustrates a number of characteristic for different sets of data from the same user as well as an average characteristic loop derived from the other loops.

It should be noted that a loop can be formed for each one of the steps captured by the sensors. An averaged loop can be derived from the various loops formed from all the steps captured by the sensors. Referring to FIG. 5, the various loops from the various steps can be seen on the plot. An average loop (see darker loop in FIG. 5) is derived from all the loops captured using the low pass filtered waveforms. Multiple methods may be used to determine the average loop. However, in one embodiment, the points for the average loop are derived by averaging the various readings for each particular time index. As such, if the data pairs are as (An[i],Bn[i]) with An[i] denoting the nth reading for sensor A at time index i and Bn[i] denoting the nth reading for sensor B at time index i, then to derive the data reading for sensor A for the average loop for time index i, one merely averages all the An[i] where n=1, 2, 3, etc., etc. Similarly, for data reading for sensor B for the average loop for time index i, one merely averages all the Bn[i] where n=1, 2, 3, etc., etc. By doing this for all the multiple time indices, an average loop is derived from all the characteristic loops.

Figure 6:
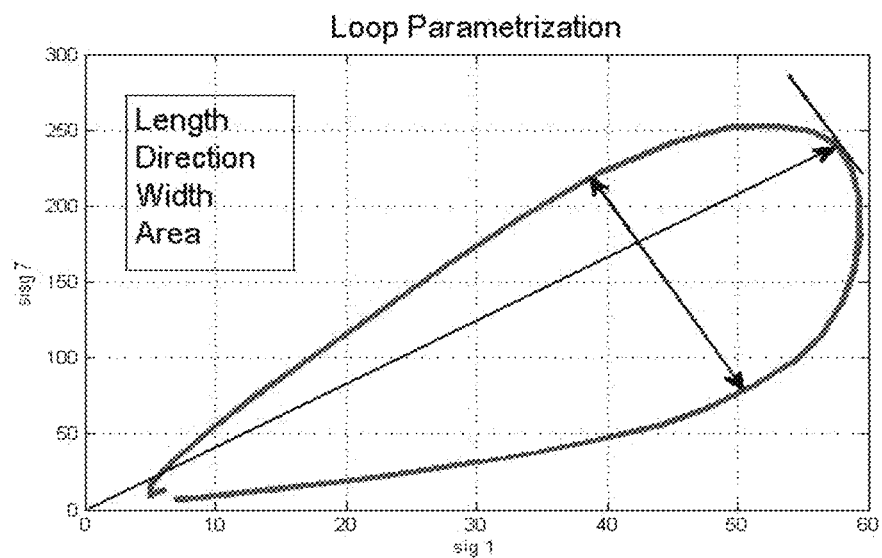
FIG. 6 illustrates the different characteristics which may be derived from the characteristic loops.

Once the average loop has been derived, the characteristics of that average loop can be determined. Referring to FIG. 6, some of the characteristics of the average loop can be seen. The length of the loop (measured from the origin), the width of the widest part of the loop, and the area occupied by the loop are just some of the characteristics which may be determined from the loop. As well, the direction of the loop (whether it develops in a clockwise or anti-clockwise manner) may also be seen as a characteristic of the loop. Another possible characteristic of the loop may be the angle between a ray from the origin to the farthest point of the loop and one of the axes of the plot. Additional characteristics of these loops may, of course, be used depending on the configuration of the system.

Figure 7:
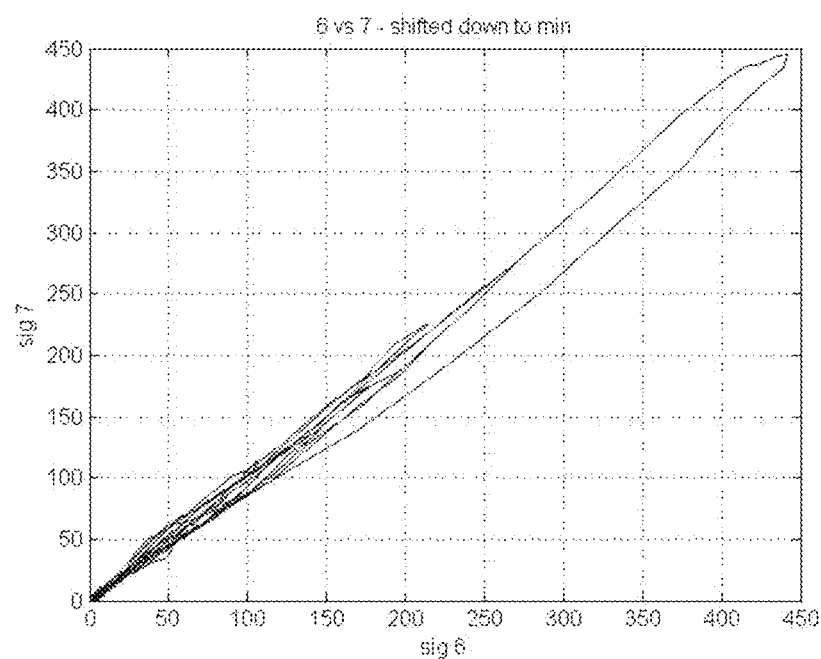
FIG. 7 illustrates characteristic loops using highly correlated data.

As another example of possible loops, FIG. 7 shows loops resulting from highly correlated data from the sensors. Such highly correlated data may produce loops that, at first glance, may not be overly useful. However, even such lopsided loops may yield useful characteristics. As an example, the amplitude from the furthest point may be used for an initial assessment of static of dynamic weight distribution.

Once the average loop for the steps captured by the sensors is determined, the characteristics for this average loop can be derived. Once derived, the same process is applied to the signature data stored in the storage module. The characteristics for the resulting signature loop (from the signature data) are then compared to the characteristics of the average loop from the data acquired from the sensors.

Figure 8:
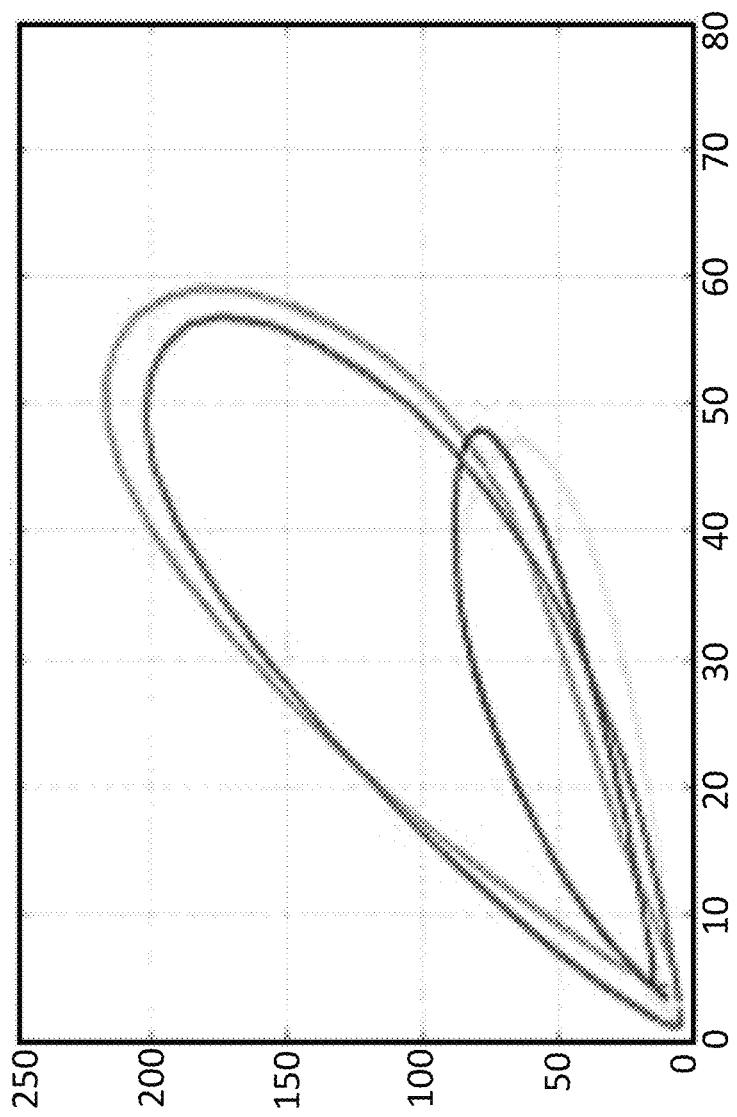
FIG. 8 shows average characteristic loops for different users.

Referring to FIG. 8, a comparison of two average loops from the gait of two individuals is illustrated. As can be seen, the characteristics of the two loops are quite different. One loop is clearly larger (more area), longer (length of loop), and wider (width at widest of the loops) than the other loop. It should be noted that custom tolerances can be applied to the comparison. Depending on the tolerance applied, the comparison can be successful (the characteristics match within the tolerances) or unsuccessful (even within the tolerances, there is no match). It should be noted that, as noted above, comparisons can be made for loops from a single user with data taken at different times. As an example, a user may have gait data taken at a first use of the system. Later gait data sets can then be taken for the same user at subsequent uses of the system. The loops derived from the initial gait data set and the subsequent gait data sets can then be compared to determine how a particular fitness program, treatment regimen, or physical condition has positively or negatively affected that user's gait over time.

Regarding tolerances, these can be preprogrammed into the system and can be determined when the signature data is gathered. As an example, a tolerance of 15% may be acceptable for some users while a tolerance of only 5% may be acceptable. This means that if the calculated characteristic of the average loop is within 15% of the calculated characteristic of the signature loop, then a match is declared. A match would indicate that there is no relevant difference between the loops being compared. Similarly, if a tolerance of only 5% is used, then if the calculated characteristic of the average loop is within 5% of the calculated characteristic of the signature loop, then a match is declared. Of course, if the calculated characteristic of the average loop is not within the preprogrammed tolerance of the calculated characteristic of the signature loop, then a non-match is declared. A non-match would indicate that there is a relevant difference between the loops being compared. A match may indicate that, for example, a fitness program, treatment regimen, or condition has not affected a user's gait between the time the first set of gait data was gathered to the time the second set of gait data was gathered. A non-match may, of course, indicate that the fitness program, treatment regimen, or condition has affected the user's gait.

It should also be noted that, in addition to the tolerances noted above, the system may use a graduated system of matches or matching. This would mean that a level of confidence may be assigned to each match, a high level of confidence being an indication that there is a higher likelihood that there is a match between the two sets of data derived from the average loop and the signature loop. A match can then be declared once the level of confidence assigned is higher than a predetermined level. A non-match can similarly be declared once the level of confidence is lower than a predetermined level. A level of indecision can be declared when the level of confidence is between the two preset levels for match and non-match. If a set of data falls within the gray area or an area of indecision between the two preset levels, then more data can be retrieved from the sensors and this data can be processed as above to arrive at a determination of a match or a non-match.

It should further be noted that, as an alternative, instead of matching or not matching two loops derived from a user's gait data, the amount of difference between the two loops can be determined. A significant difference between the characteristics of the two loops, preferably derived from data gathered from the same user using the same sensors in the sensor module at different times, would indicate a change of some sort. A significant difference between such two loops would indicate a significant change from the time the first data set was gathered to the time the second data set was gathered. As noted above, this could indicate that a fitness program, treatment regimen, or condition was having an effect on the user's gait. It may also indicate that a user's physical or medical condition is either progressing or regressing. The characteristics for which a difference may be found may, as noted above, include the size of the loops, the angle of the loops to one of the axes of the plot, the perimeter of the loops, the area covered by the loops, as well as other characteristics. A tolerance may, of course, be built into the comparison subroutine. As an example, if the tolerance is set at 2%, if a characteristic of two loops are within 1% (i.e. less than 2%) of each other (e.g. the sizes of the two loops) then no difference is concluded.

For greater clarity, the difference between two loops may be quantified and, depending on how great the differences are, alarms or other steps may be taken. As an example, if the area of a loop derived from a user's initial data set is compared with the area of a loop derived from a data set gathered a few months later, the differences may be significant. If there is no appreciable difference, then one can conclude that no change has occurred in the user's condition. If, on the other hand, the second data set has a much larger area (e.g. 25% greater area than the area covered by the loop from the first data set), this may indicate that the user is walking slower or that the user is placing more pressure on his feet with each step. Depending on the user's physical condition, this may indicate a progression (getting worse) or a regression (getting better) of that condition. It may also indicate that a fitness program or treatment regimen being used may not be effective. A threshold may thus be programmed so that if the difference in value of a characteristic being compared between two loops exceeds a specific amount or percentage, an alarm may be activated.

Regarding the programming or storage of the signature or characteristic data into the system, this is preferably done when the user first registers and wears the insole component of the system. This first data set can provide a baseline set of data to be used in comparison with subsequent data sets. This is done by having the user use the insole/sensor module by taking a specific number of normal steps. These steps are then captured in the system and are stored as signature/characteristic or baseline data. Once stored, the signature data can be retrieved and various characteristics of the signature data (by way of the signature loop) can be determined as described above. As described above, the signature data stored may take any number of forms. The signature data may be the raw data gathered from the user when s/he took the specific number of normal steps. Alternatively, the signature data may be the filtered version of the raw data or it may be the various characteristics of the various possible signature loops. Also, instead of the raw data which forms the waveforms, the waveforms themselves may be stored as signature data. The signature data may take any form as long as the characteristics of the signature loops may be derived from or be extracted from the signature/characteristic/baseline data.

Figure 8A:
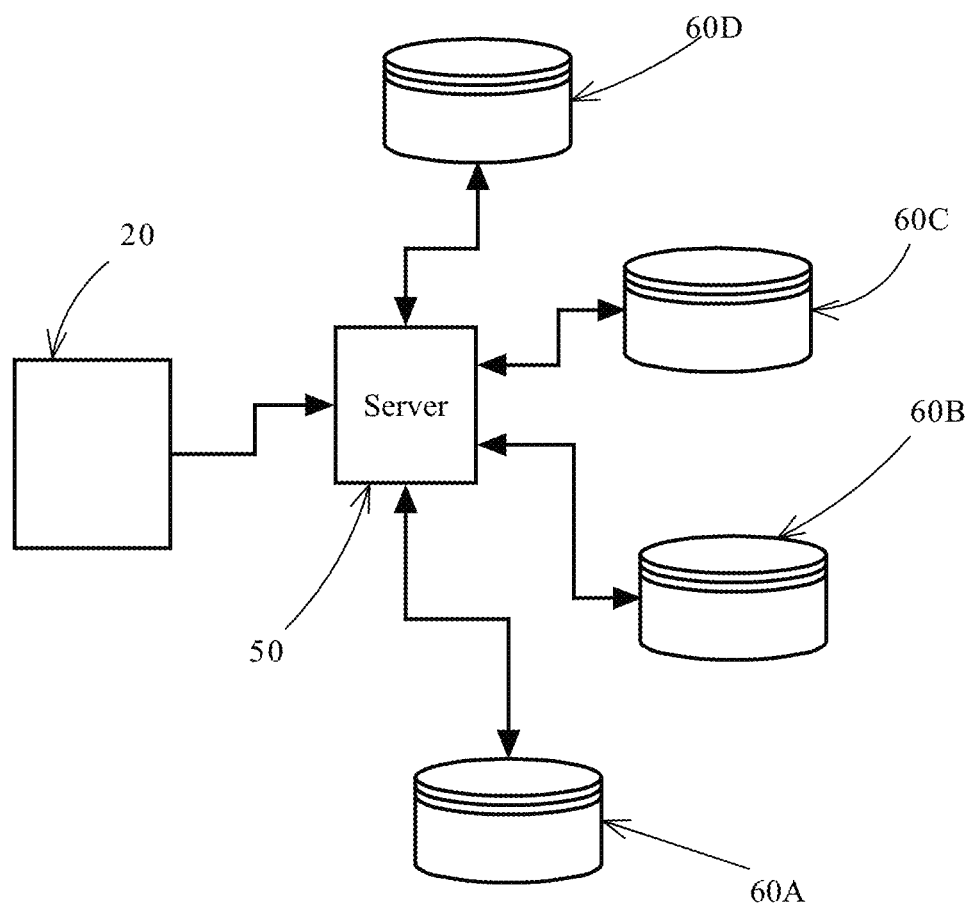
FIG. 8A is a block diagram illustrating the data connections between various components of the system according to another aspect of the invention.

As noted above, the system may include a server and a network of distributed databases connected to that server. The data gathered by the insole may be transmitted to either the server or to the databases. Such a server or its connected network of distributed databases may, to assist in the diagnosis of the user's condition for example, be used to consult with at least one medical or fitness database. Referring to FIG. 8A, a block diagram illustrating the connections between the various parts of the system is illustrated. As can be seen from FIG. 8A, the user's insole data gathering sub-system 20 communicates with a server 50. The server 50 serves as the main data processing and analytical unit to determine for example the user's physical or medical condition based, at least in part, on the data gathered from the user's gait. After the server receives gait data or the characteristic data from the insole 20 (perhaps from two insoles), this can be used by the server to determine the user's physical or medical condition. This includes determining the condition's progression, regression, or development. This may be performed by referring to one or more medical or fitness databases 60A, 60B, 60C, 60D. The server may receive both structured and unstructured data from the databases and/or from the user's insole. Preferably, the databases contain data relating to disease pathology, human performance, workforce industrial safety, human kinetics, sports performance, post-operative rehabilitation, therapeutics, and/or biometric data relating to injury and disease pathologies including conditions such as diabetes, Parkinson's disease, dementia, aging, and other vestibular disorders.

To assist the server in determining a diagnosis and/or a determination of the progression, regression, or change in the user's condition, the following characteristics of the user may be entered into the server and may be taken into account in any analysis: a foot type, general health, fitness level, type of gait, height, weight, age, gender, and/or nationality. Data entry into the server may be effected using various well-known means. As an example, such data may be transferred from a user's profile to the server. The server may then take such user data, in conjunction with the gait-based and gait-derived data, and analyze such data with data from the various databases. Then, based on the input from the various databases and the gathered data for the user, the server can produce its output.

The server's output may include an indication that the user's condition has regressed, progressed, is abnormal, or is normal. Similarly, the output may indicate the pathologies operative with the user as well as an indication if the user requires or is using corrective orthotics.

It should be noted that the user's foot characteristic may be one of: Egyptian, Roman, Greek, Germanic, or Celtic. Similarly, the user's foot type may be one of: flat arch, medium arch, or high arch. The user's type of gait may be one of: normal, toe in or toe out, knee in or knee out, lean forward or lean backward, posture easy or posture rigid, and trunk sway. The user's health and/or fitness may be categorized as one of: athletic, fit, average, below average, poor, or one where the user has a reported illness or disease.

Figure 9:
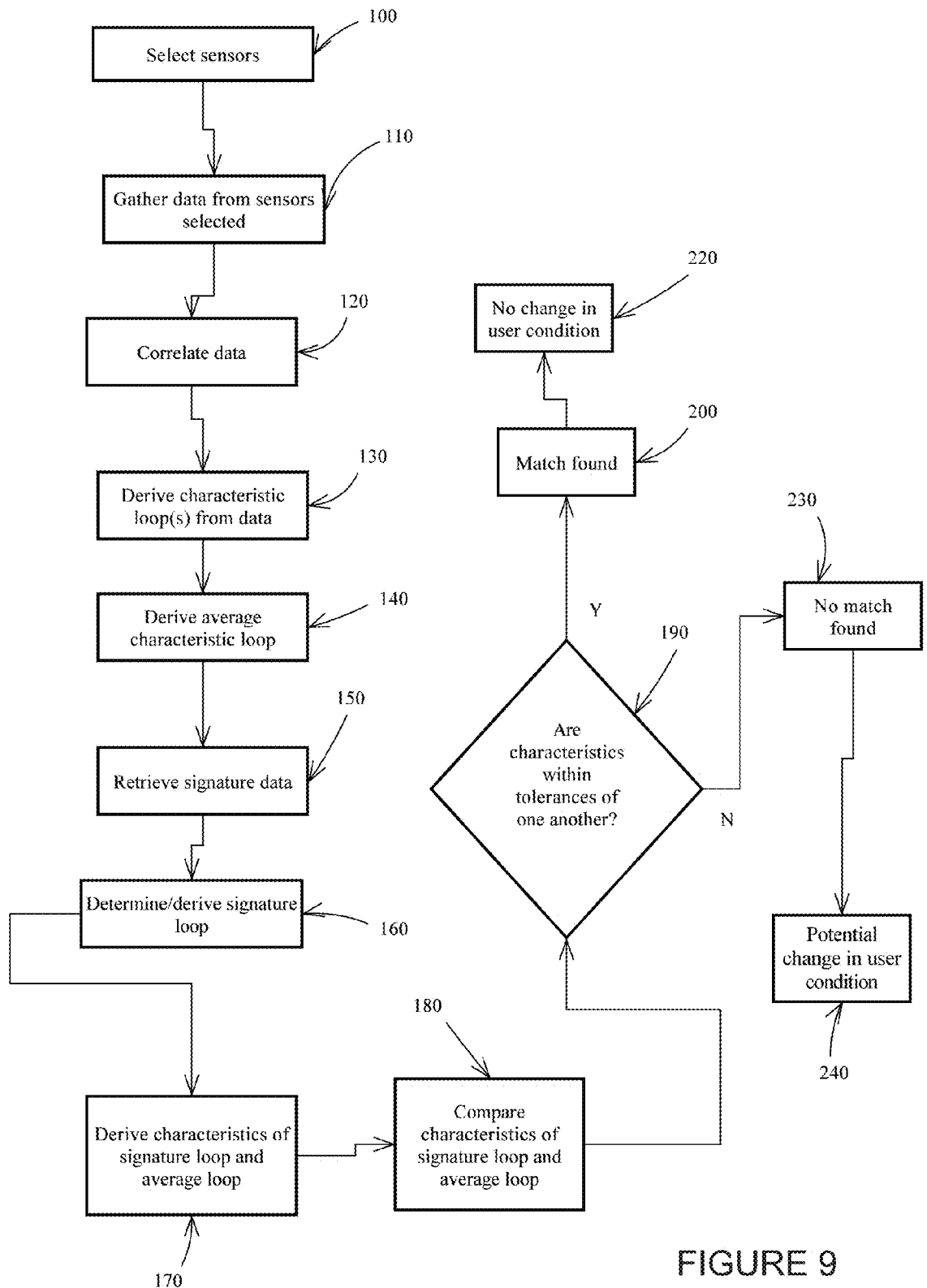
FIG. 9 is a flowchart illustrating the steps in a method according to another aspect of the invention.

Referring to FIG. 9, a flowchart of the process described above is illustrated. To store the signature data into the system, the initial step 100 in the process is that of selecting two of the sensors to be used in the comparison process. As noted above, the sensors are, in one embodiment, inserted or installed in a user's shoe. Once the sensors have been selected, data is gathered from these sensors as the user walks normally (step 110). Once gathered from the sensors, the data is then correlated with one another to form the data pairs noted above (step 120). This means that data points from one sensor is mated with data points from another sensor. With the data pairs in hand, at least one characteristic loop can then be created/derived from the data pairs (step 130). Depending on the configuration, discrete steps may be separated from one another so that each step may have its own characteristic loop. Alternatively, an average characteristic loop may be derived from the data values from the sensors. Once the average characteristic loop has been found (step 140), the signature data can be retrieved (step 150). The signature data, depending on configuration can then be used to determine the signature loop (step 160). The characteristics of both the average characteristic loop and the signature loop can then be calculated or derived from the two sets of data (step 170). The characteristics are then compared (step 180), taking into consideration the preprogrammed tolerances. If the characteristics from the two sets of data are the same (step 190) (within the preprogrammed tolerances) then a match is found (step 200) indicating no change in the user's condition (step 210). If they are not within the preprogrammed tolerances, then no match is found (step 220) and a potential change in the user's condition is indicated (step 230). The indication of whether a match is found or not found can then be communicated with the server 50. The server 50 may then communicate with the distributed databases to gather data and/or correlations between the user's characteristic data and potential/actual medical and/or physical conditions.

The process may also be seen as eight specific steps.

The first processing step after retrieving the data is one where the pair sensor signals are filtered applying DFT (Discrete Fourier Transform) based low-pass filter. The cut-off frequency of the filter is defined taking into account a Nyquist frequency (related to the sampling rate) on the high end, and a main signal frequency (related to the walking speed of the individual) on the low end. Walking frequency estimation is also a part of the described processing step.

Using an FFT (Fast Fourier Transform) implementation technique and sync-filter as a benchmark, a low pass filter with flat pass-band (low ripple) high stop band attenuation may be used. Additional advantage is taken from the use of non-causal filters since the hard-real-time processing is not required (signals are registered first and then filters are applied).

The second processing step is a construction of the characteristic loop for the chosen pair of signals. The characteristic loop is an ordered set of points with coordinates $(X(i),Y(i))$ where $X(i)$ is a first chosen signal and $Y(i)$ is a second chosen signal, i is an index corresponding to the sample number.

An autonomous loop is constructed for the time period (subset of all samples) corresponding to the evolution of both signals from low level to maturity level and back to low level. Such a construction is possible since the low level of all signals have a non-empty intersection corresponding to the foot not contacting the ground.

Due to quasi-periodicity of all signals resulting from the nature of human walking, characteristic loops can be constructed autonomously for several periods in time. Although initially defined for raw signals, autonomous loops can then be constructed for smoothed signals (obtained after the first step processing described above).

The third processing step is that of averaging the loops. Several loops are constructed according to the recording of several steps while the person is walking. Those steps and respectively those loops are subject to significant variations. It has been found that only the average loop provides a stable and robust characteristic of human walking.

Averaging of the loops is done by artificially synchronizing several loops (as corresponding to several steps) followed by weighted averaging of the synchronized loops. Weight factors are computed according to the phase shifts from an estimated reference signal (main walking frequency—as per first processing step).

The fourth processing step consists of extracting initial geometrical parameters from the average loop such as loop length, loop width, direction of longitudinal axes, loop directionality (clockwise or counter-clockwise) and the area inside the loop. Other characteristics/parameters which can be used are the variance of each parameter listed above as computed for individual walking steps and as compared to the average value (computed from average loop).

Other parameters which can be extracted may use:
Geometrical method—identify a point on the loop farthest from the origin (let us call it M) this point is further used to find the length (|OM|) and direction of the longitudinal axis (OM), the width is defined as maximal projection onto the line perpendicular to OM
Statistical approach—considering the loop as the cloud of points, the elliptical fit (correlation analysis) can be applied followed by extraction of the parameters of the fitted ellipse (major and minor axis length and orientation).

Regarding loop directionality, the directionality of the loop is related to the phase shift between signal Y and signal X. Namely, the loop is clockwise if Y signal grows from low level to maturity first, followed by the growth of X signal.

The fifth processing step consists of analysing special cases. It is worth noticing that in some cases, for some pairs of signals, the construction of the loop as described above might yield less than perfect results. This may result in a "degenerated loop" due to a high correlation between signals. The "loop" in such case is located very close to the diagonal. For this case only the point farthest from the origin is actually computed (corresponding to maximal amplitude of both signals).

The sixth processing step consists of comparing the loops computed from 2 separately recorded data. It has been found that the high discrimination efficiency of the proposed parametric representation of the pair-wise average loops (see FIG. 8 as an example). Namely, for several pairs of signals/sensors extracted from the set of 8 signals/sensors, the average loops constructed from the smoothed signals stably demonstrate significant similarities when constructed from the data corresponding to the same individual as well as significant differences from average loops constructed for different individuals.

The seventh processing step consists of combining the results of the comparison of several (up to all 56 possible pairs from 8 different sensors/signals) pairs in order to produce a highly efficient discriminate function. Results from various pairs are first weighted according to the number of parameters that can be robustly estimated to support the comparison of the loops. Finally, the results from various pairs can be fused using Dempster-Shaefer framework for an estimation of the likelihood that loops from the baseline data and the gathered data are similar or not.

In addition to the above processing steps, it should be noted that, for mobility-impaired-based applications, the data gathered can be expected to have a number of behaviours. The characteristics that are extracted when performing the loop signature computation (see above) can be divided in three classes:

A) (Class-1) Dimensionless parameters such as:
(1) loop directionality,
(2) direction of longitudinal axes of the loop,
(3) loop elongation (e.g. major to minor axis ratio), etc., as well as standard deviations of those parameters computed over all of the collected data.

B) (Class-2) Size-type parameters having a single dimension such as:
(1) loop length,
(2) loop width,
(3,4) major and minor axis of elliptical approximation of the loop (see above), etc. as well as standard deviations of those parameters computed over all of the collected data.

C) (Class-3) Area-type parameters having two dimensions such as:
(1) area of the loop,
(2) product of major and minor axis of elliptical approximation of the loop and variance of those parameters computed over all of the collected steps.

These 3 classes of the parameters can be used in different ways in determining the estimation of differences between data sets. For processing the data sets based on mobility impairments, stride length, stride to stride variability, cadence, and other movement data can affect class 1 and 2 data sets while weight, posture and other similar physiological changes can affect class 3 parameters.

As an example of how physical changes can affect the characteristics of the derived loops, one can look at the effects of weight-based differences. For such differences, dimensionless parameters (Class-1) are expected to be invariant to weight changes. Size-type parameters (Class-2) are expected to be proportional to the weight change reflecting the fact that the loop is stretched or contracted according to the weight change factor (i.e. the ratio of newly estimated weight to the older one). Area-type parameters (Class-3) are expected to be proportional to the square of the weight change factor.

For processing of weight change-based data, the processing steps can be summarized as:
1. Extraction of the data pairs that provide the robust estimation of relevant parameters;
2. Estimation of the weight change factor from the class-2 (direct) and class-3 (as square root) parameters and verification of invariance of class-1 parameters;
3. Determination of the hypothetical (average) value of the weight or physical characteristic factor;
4. Analysis of the result based on Dempster-Shaefer framework in order to estimate the likelihood that the gathered data supports the determined value.

Of course, the above steps can also be used to process data to determine changes in gait-based data due to other physiological changes. In step 2, instead of estimating the weight change factor, the change factor due to the physiological change can be performed and verifying that some other parameters are invariant.

It should also be noted that a data histogram of daily loop signatures can be stored in the storage module and can be periodically re-correlated to form a new biometric loop signature which reflects the user's weight gain or loss.

The system described above may be used in any number of ways. The system can be used to determine a user's physical or medical condition as well as whether a fitness program or treatment regimen is effective or not. As is well known, for some physical and medical conditions, the progression of the condition affects a person's gait. Similarly, the regression of the condition also affects the person's gait. As such, by comparing a user's baseline gait data with subsequently gathered gait data, the user's condition can be monitored. If no change in the user's gait is detected, then the physical or medical condition has neither progressed nor regressed. If there is a noticeable change in the user's gait (as evidenced by differences in the loops derived from the baseline gait data and the subsequent gait data) this may indicate progression, regression, efficacy of a fitness program or treatment regimen, or any number of health changes in the user. This determination can additionally be performed by the server, perhaps in conjunction with input from the various databases noted above. As well, the determination may be performed after human verification and checking of the data provided. This determination may be made in conjunction with other clinical tests so as to determine correlation between the loop differences, the types of differences, the amount of the difference, and the different conditions and changes in the condition.

In another embodiment, all of the data processed by the data processing module may be internally encrypted so that external systems would not be privy to the raw data transferred between the sensor module and the data processing module. Prior to transmitting the raw data from the sensor module to the data processing module, the data may be automatically encrypted. As can be understood, the data processing module may be physically remote from the sensor module and, as such, the data transmissions between these modules may be vulnerable to the outside. In another embodiment, the data processing module is contained within the insole to ensure that any data transfers between the modules are slightly more secure.

In another embodiment, any data transfers or communications between the system and any outside server or network systems are encrypted, preferably with one time encryption schemes, to ensure that outsiders are not able to intercept any usable data. Such precautions would preserve the system user's privacy.

The system of the invention may be used to periodically determine if a user's physical or medical condition is progressing or regressing. As well, it may be used to determine if any fitness program or treatment regimen to which the user is being subjected to has had an effect on the user or on the user's gait. The user's baseline gait data may be gathered when the user first visits a facility properly equipped with the system of the invention. Subsequent visits by the user would entail gathering subsequent gait data sets. The loops derived from the baseline gait data set and the subsequent gait data sets can be compared with one another to view any variances between the user's gait data. The amount of change in the loop characteristics from the different data sets can provide an indication as to the degree of change in the user's condition. Large changes in the loop characteristics may indicate an acceleration in the user's condition and may also indicate whether the user's fitness program or treatment regimen (which may include pharmacological treatments) is effective or not.

It should be noted that any useful data processing means may be used with the invention. As such, ASICs, FPGAs, general purpose CPUs, and other data processing devices may be used, either as dedicated processors for the calculations or as general purpose processors for a device incorporating the invention.

The method steps of the invention may be embodied in sets of executable machine code stored in a variety of formats such as object code or source code. Such code is described generically herein as programming code, or a computer program for simplification. Clearly, the executable machine code may be integrated with the code of other programs, implemented as subroutines, by external program calls or by other techniques as known in the art.

The embodiments of the invention may be executed by a computer processor or similar device programmed in the manner of method steps, or may be executed by an electronic system which is provided with means for executing these steps. Similarly, an electronic memory means such computer diskettes, CD-Roms, Random Access Memory (RAM), Read Only Memory (ROM) or similar computer software storage media known in the art, may be programmed to execute such method steps. As well, in another embodiment, electronic signals representing these method steps may also be transmitted via a communication network to a network of distributed databases for individual, group or population based analytics by characteristic definition.

Embodiments of the invention may be implemented in any conventional computer programming language For example, preferred embodiments may be implemented in a procedural programming language (e.g."C") or an object oriented language (e.g."C++"). Alternative embodiments of the invention may be implemented as pre-programmed hardware elements, other related components, or as a combination of hardware and software components.

Embodiments can be implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or electrical communications lines) or a medium implemented with wireless techniques (e.g., microwave, infrared or other transmission techniques). The series of computer instructions embodies all or part of the functionality previously described herein. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server over the network (e.g., the Internet or World Wide Web). Of course, some embodiments of the invention may be implemented as a combination of both software (e.g., a computer program product) and hardware. Still other embodiments of the invention may be implemented as entirely hardware, or entirely software (e.g., a computer program product).

A person understanding this invention may now conceive of alternative structures and embodiments or variations of the above all of which are intended to fall within the scope of the invention as defined in the claims that follow.

We claim:

1. A method for determining changes in a user's condition, the method comprising:

a) in a single insole worn by a user, the insole having a plurality of sensors for gathering gait-based pressure data and having at least one processor, using said at least one processor to select a first sensor and a second sensor from said plurality of sensors, said plurality of sensors being in said insole and each of said plurality of sensors being a discrete force sensor that detects an amount of force or pressure exerted on a section or region of said insole;
b) using said at least one processor to gather pressure data from each of said first sensor and said second sensor selected in step a), said pressure data being for a single step of said user;
c) using a server connected to at least one database and remote from said insole to correlate data gathered from said first and second sensors such that data points gathered from said first sensor and from said second sensor at similar instances are matched with each other to result in data point pairs, each data point pair having a first data point gathered from the first sensor and a second data point from the second sensor;
d) using said server to determine at least one characteristic loop from said data point pairs, each characteristic loop being a loop formed when said data point pairs are plotted such that data points from said first sensor are on one axis and data points from said second sensor are on another axis, each one of said at least one characteristic loop having at least one geometric parameter extractable from said at least one characteristic loop;
e) using said server to retrieve signature characteristic data, said signature characteristic data being previous pressure data resulting from biometric data previously gathered from said user, said signature characteristic data being pressure data previously gathered from said first sensor and from said second sensor for a previous single step of said user, said signature characteristic data being previous data point pairs previously gathered from said first sensor and from said second sensor, each previous data point pair having a previous data point from said first sensor and a previous data point from said second sensor;
f) using said server to determine a signature characteristic loop from said signature characteristic data, said signature characteristic loop being a loop formed when said previous data point pairs are plotted such that previous data points from said first sensor are on one axis and previous data points from said second sensor are on another axis, said signature characteristic loop having geometric parameters extractable from said signature characteristic loop;
g) using said server to calculate said geometric parameters from said at least one characteristic loop and from said signature characteristic loop, wherein said geometric parameters include at least one of:
a length of said loops;
a width of said loops;
an angle of said loops with a given axis;
a direction of propagation of said loops; and
an area of said loops;
h) using said server to calculate a difference between a first geometric parameter calculated from said at least one characteristic loop and a second geometric parameter calculated from said signature characteristic loop;
i) comparing said difference with predetermined limits;
j) if said difference calculated in step h) is not within said predetermined limits, using said server to determine that a change has occurred in said user's condition;
k) if said difference calculated in step h) is within said predetermined limits, using said server to determine that a change has not occurred in said user's condition.

2. The method according to claim 1, wherein step d) comprises using said server to determine multiple characteristic loops using multiple sets of pressure data gathered from said first and second sensors selected in step a) and averaging said multiple characteristic loops to result in an average loop.

3. The method according to claim 2, wherein differences between said geometric parameters of said average loop and said geometric parameters of said signature characteristic loop are calculated in step h).

4. The method according to claim 1, wherein said server filters said pressure data gathered from said first and second sensors prior to producing said data point pairs.

5. The method according to claim 1, further including a step of using said server to receive data input relating to said user's physical characteristics.

6. The method according to claim 5, wherein said user's physical characteristics includes at least one of:
a foot type;
general health;
fitness level;
type of gait;
height;
weight;
age;
gender; and
nationality.

7. The method according to claim 1, further including a step of using said server to receive input from at least one health or fitness-based database concerning said user's condition.

8. The method according to claim 7, wherein said input is based at least on at least one of said user's physical characteristics, said user's physical characteristics being at least one of:
a foot type;
general health;
fitness level;
type of gait;
height;
weight;
age;
gender; and
nationality.

* * * * *